United States Patent [19]

Becht

[11] Patent Number: 4,493,322
[45] Date of Patent: Jan. 15, 1985

[54] SURGICAL STAPLING INSTRUMENT

[75] Inventor: Carl T. Becht, Cincinnati, Ohio

[73] Assignee: Senco Products, Inc., Cincinnati, Ohio

[21] Appl. No.: 425,542

[22] Filed: Sep. 28, 1982

[51] Int. Cl.³ .................. A61B 17/04; B31B 1/00
[52] U.S. Cl. .................. 128/334 R; 227/19; 227/DIG. 1
[58] Field of Search .......... 128/334 R, 337; 227/DIG. 1 A; 29/243.56

[56] References Cited

U.S. PATENT DOCUMENTS

| 3,077,812 | 2/1963 | Dietrich | 35/49 |
| 3,160,890 | 12/1964 | Lefebure | 29/243.56 |
| 4,259,251 | 3/1981 | Moshofsky | 128/334 R |
| 4,375,866 | 3/1983 | Giersch et al. | 128/337 |
| 4,391,402 | 7/1983 | Campbell et al. | 128/334 R |

Primary Examiner—Dalton L. Truluck
Assistant Examiner—Gene B. Kartchner
Attorney, Agent, or Firm—Frost & Jacobs

[57] ABSTRACT

A surgical stapling instrument for forming and implanting surgical staples in the tissue of a patient to close a wound or incision therein. The instrument comprises a body. A row of staples is mounted within the body. A feeder assembly is provided to constantly urge the row of staples forwardly, to locate the forwardmost staple thereof in position to be formed. A pair of staple formers are pivotally mounted on the body and are rotatable between normal retracted positions and staple forming positions wherein they form the forwardmost staple of the row and implant the staple in the tissue of the patient. A pair of levers are pivotally affixed to the body of the surgical stapling instrument to shift the formers to their forming positions and a resilient member is provided to bias the formers to their normal retracted positions.

10 Claims, 19 Drawing Figures

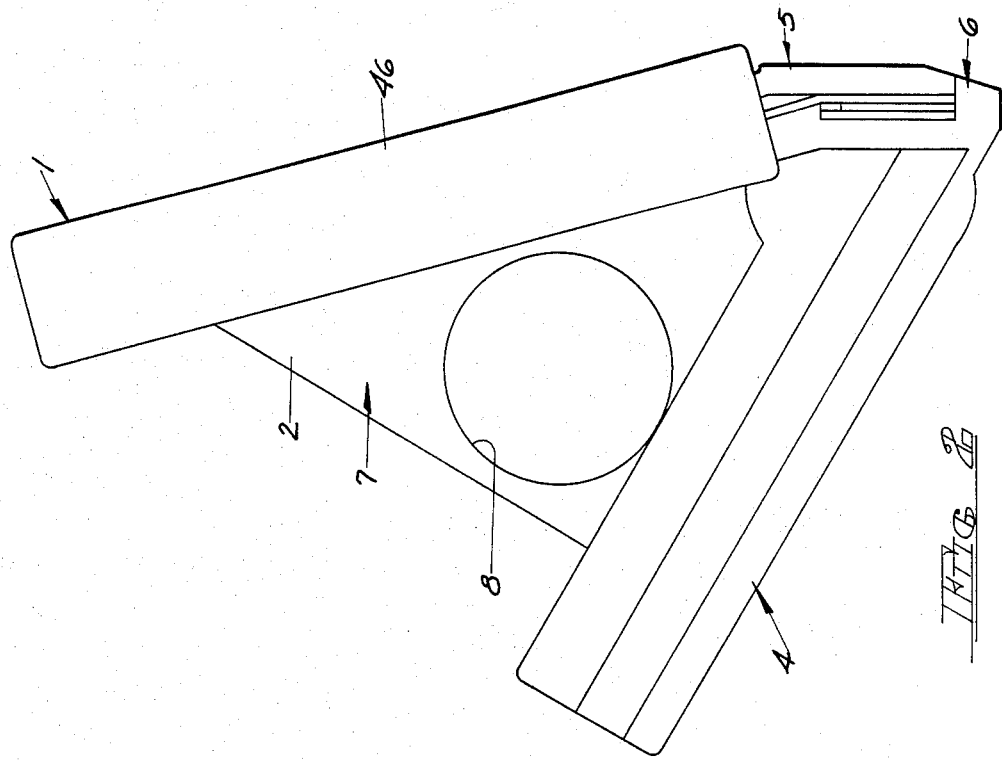
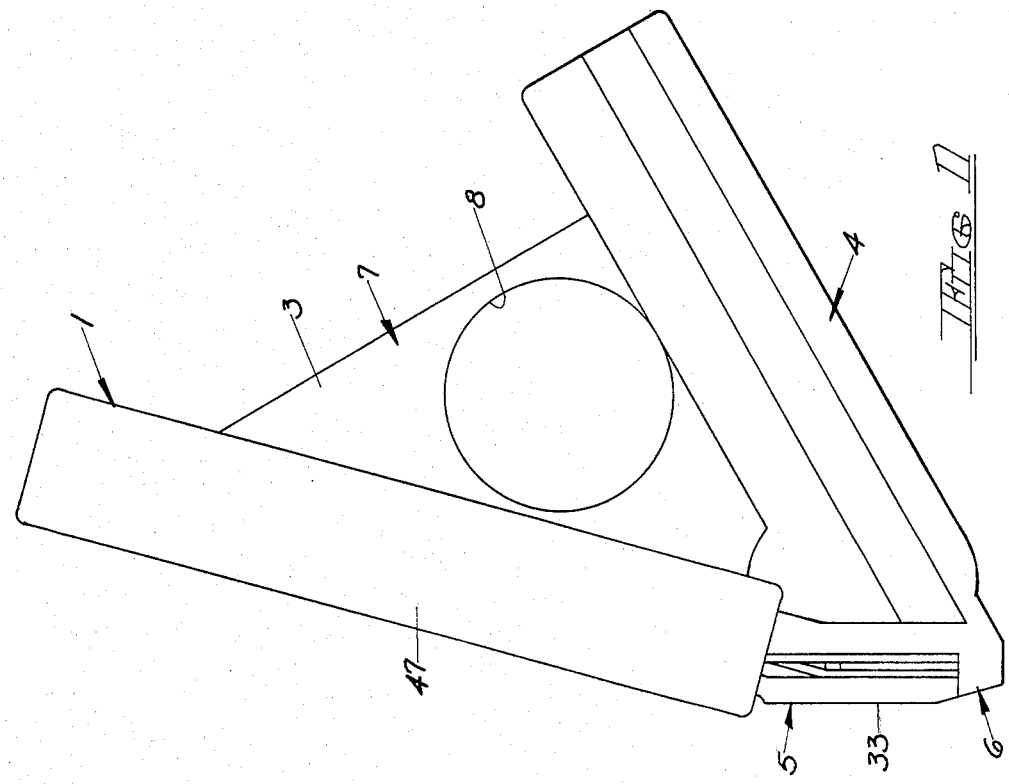

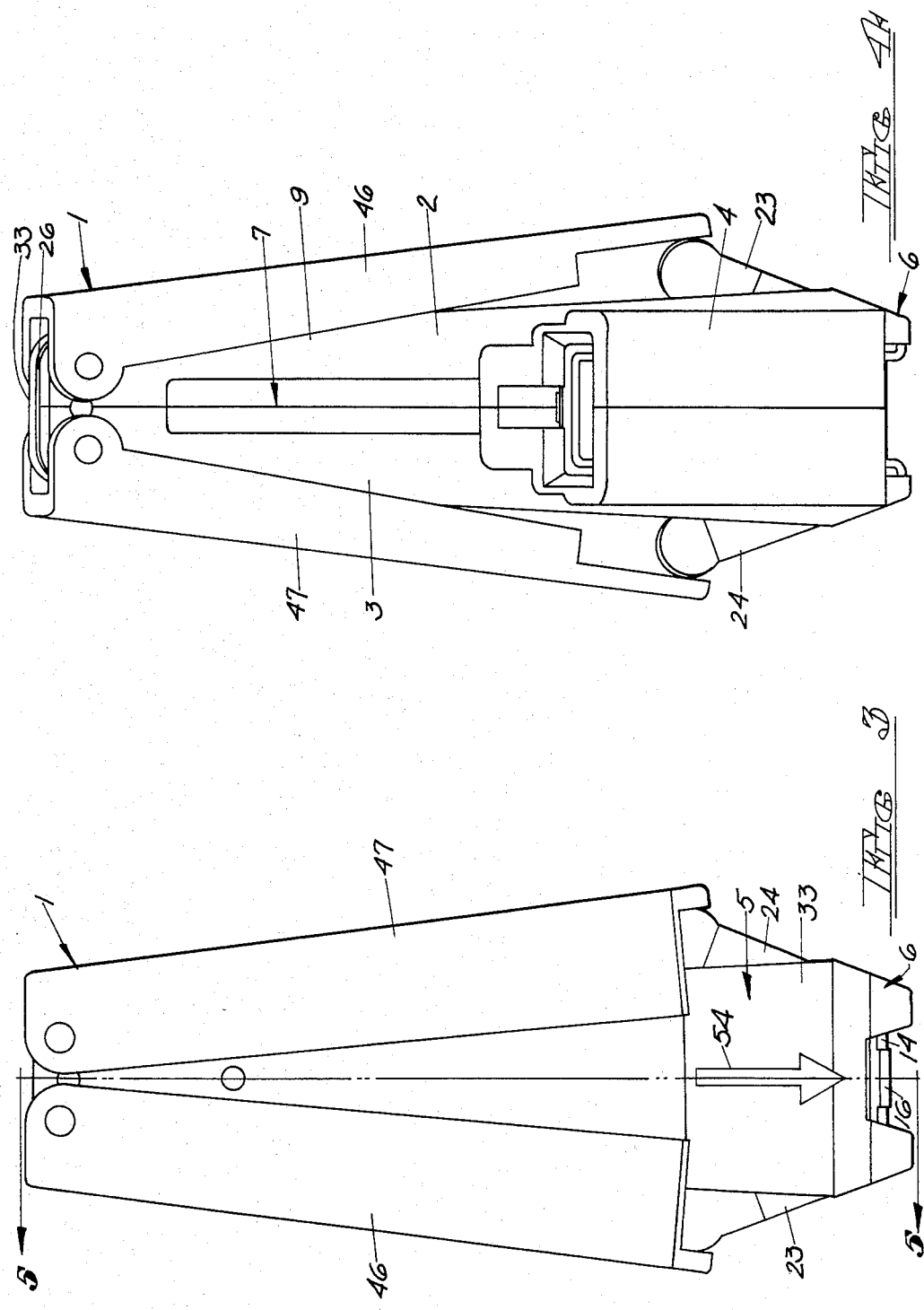

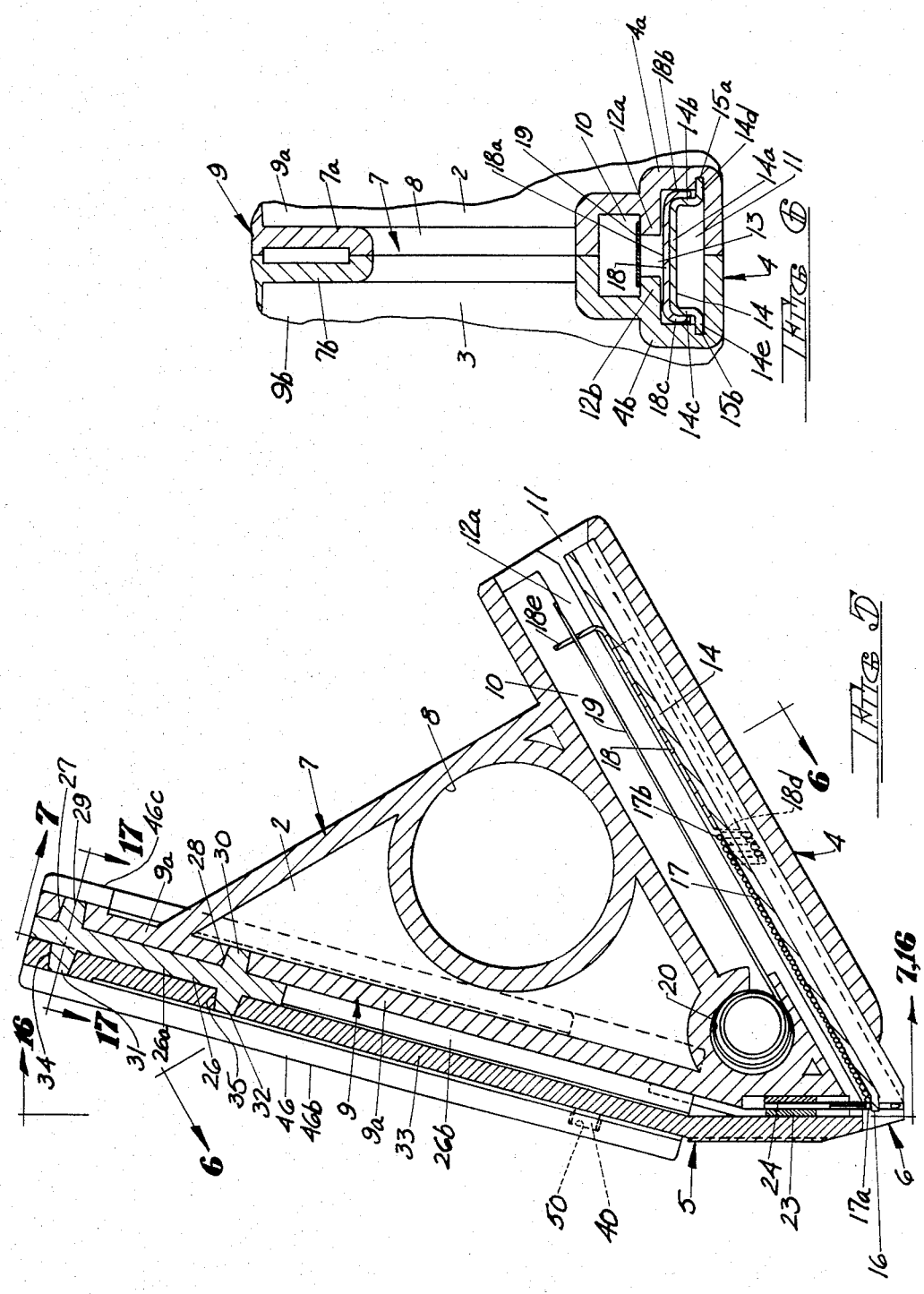

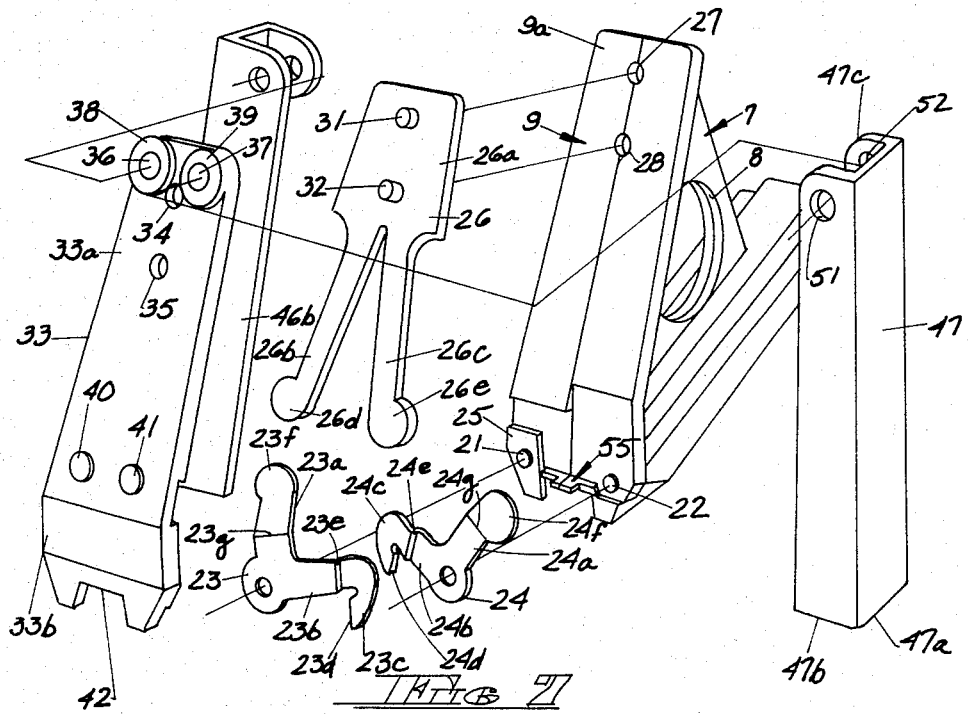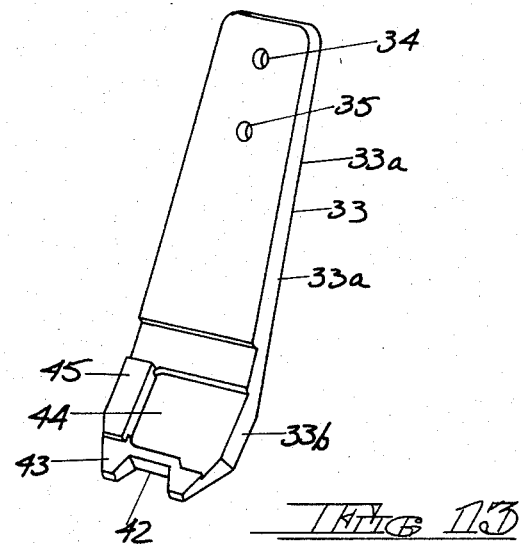

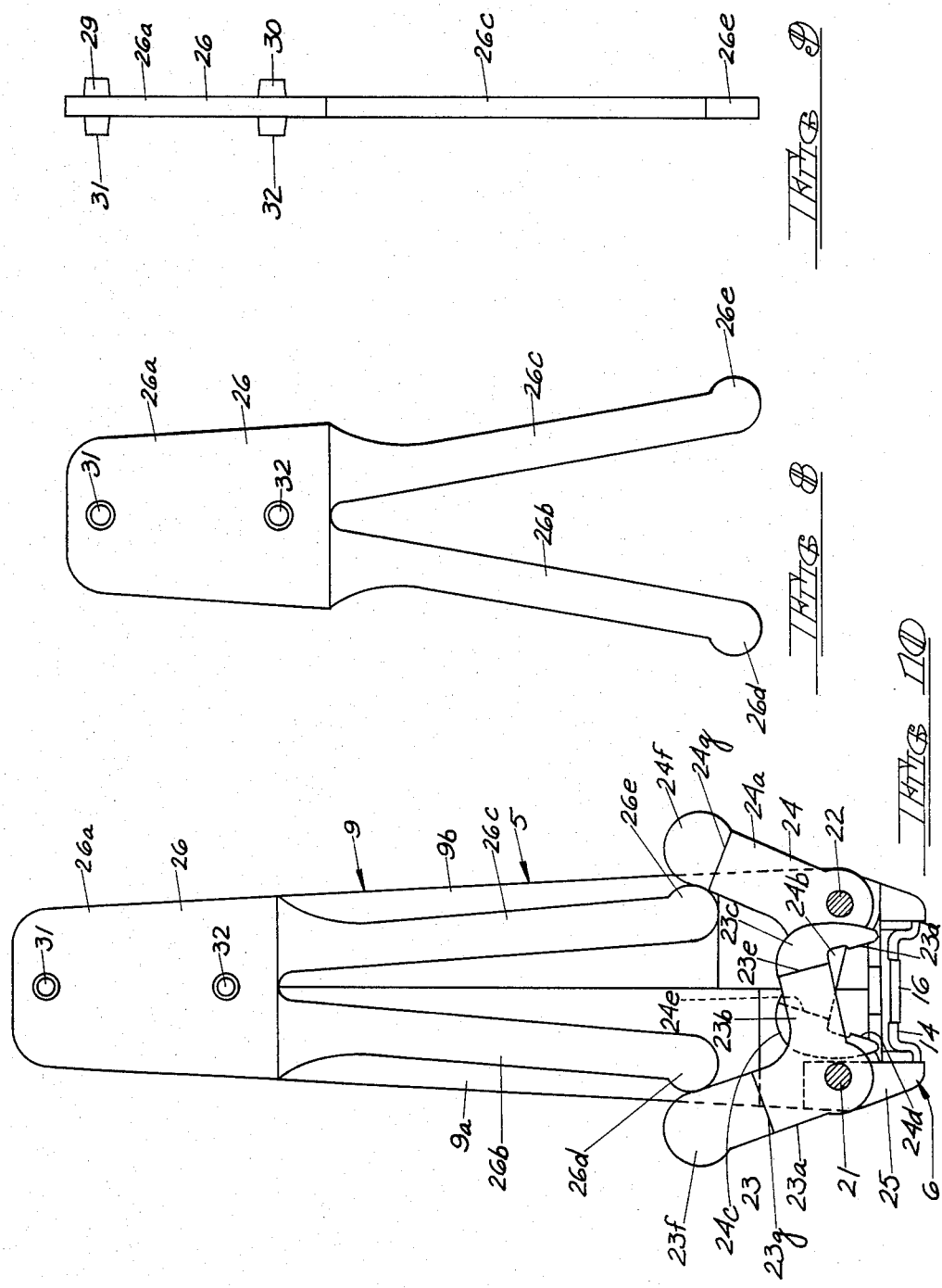

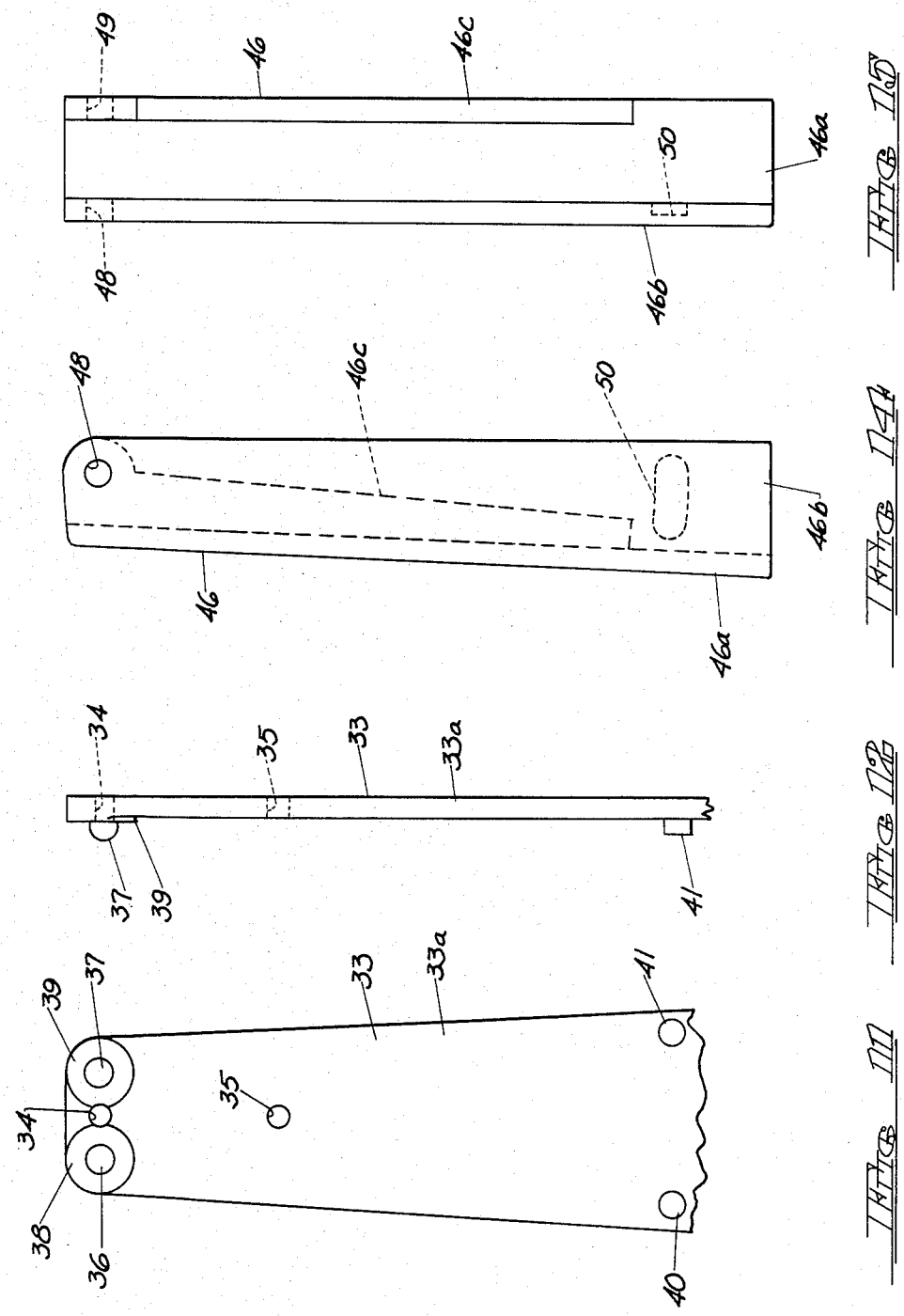

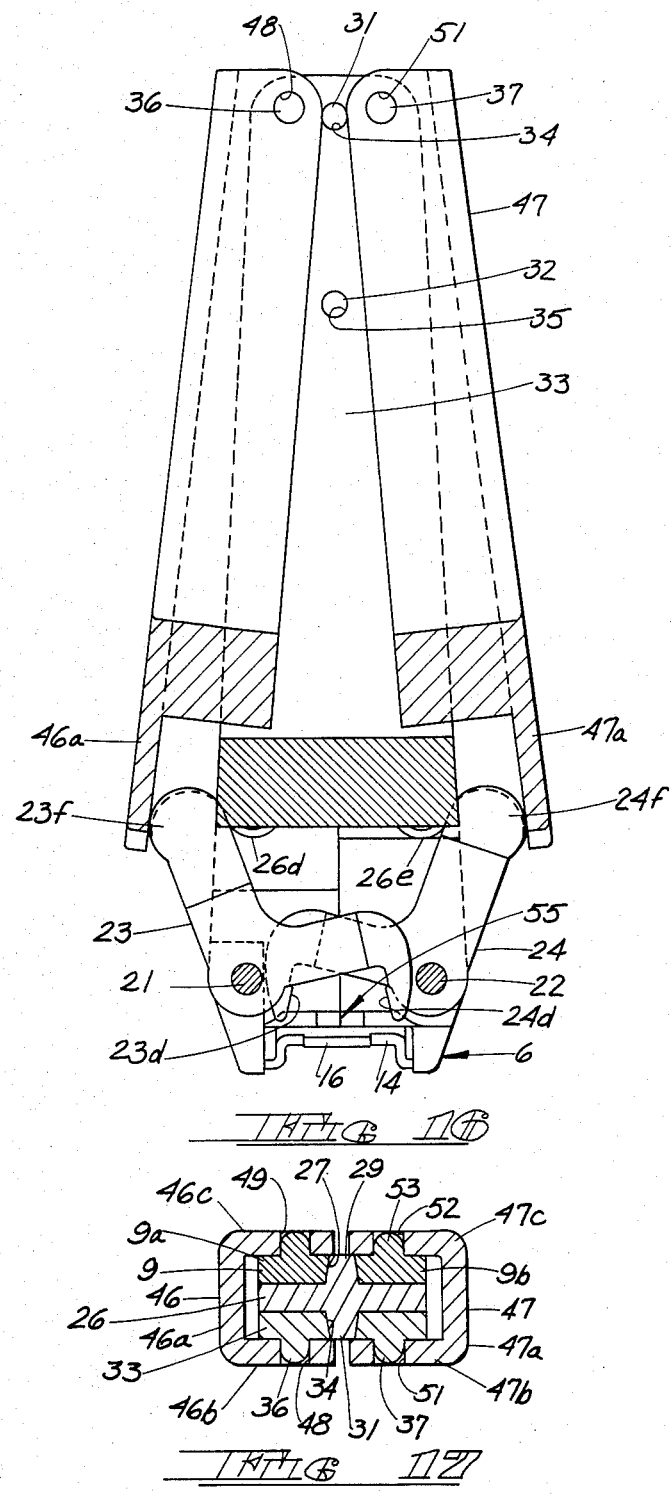

SURGICAL STAPLING INSTRUMENT

TECHNICAL FIELD

The invention relates to a surgical stapling instrument, and more particularly to such an instrument having a pair of pivotally mounted staple formers, rotatable so as to cause a surgical staple to be formed in the tissue of a patient.

BACKGROUND ART

The stapling instrument of the present invention may have many applications where it is desirable to implant and form a staple from one side only of the item being stapled. The stapling instrument is, however, particularly adapted for use as a surgical stapling instrument and will, for purposes of an exemplary showing, be so described. The surgical stapling instrument of the present invention could be constructed so as to be reusable, as will be briefly discussed hereinafter. Nevertheless, it is particularly well adapted to be inexpensively produced as a single-use, disposable instrument, and for that reason it will be so described.

In recent years surgeons have come more and more to the use of surgical staples (sometimes referred to as staple sutures), rather than conventional thread sutures, for the closing of wounds or incisions in the tissue of a patient. This is true in part because the use of surgical staples is a far easier procedure. Of even greater importance, however, is the fact that the use of surgical staples is very much faster, thus reducing the time required for suturing. This, in turn, reduces the length of time a patient must be maintained under anesthesia.

Prior art workers have developed various types of surgical stapling instruments, examples of which are taught in U.S. Pat. Nos. 3,618,842; 3,643,851; 3,717,294; 3,836,555; and 3,873,016. In general, these prior art surgical stapling instruments are complex in construction and expensive to manufacture. They do not lend themselves well to be constructed as disposable instruments. Such prior art surgical stapling instruments generally require a replaceable cartridge for the staples and a portion of the force necessary to actuate these instruments is expended in shifting a staple from a row thereof within the cartridge to a forming means, prior to the formation of the staple.

Prior art workers have also devised numerous types of surgical clip applicators having forcep or tweezer-type clip-bending arms. Examples of such structures are taught in U.S. Pat. Nos. 1,203,269; 2,096,173; 2,256,382; 2,733,441; 2,744,251; 2,789,288; 3,047,874; 3,152,336; and 3,775,826. The last mentioned patent is of interest in that it teaches a disposable wound clip applicator. U.S. Pat. No. 1,203,270 teaches a wound clip forceps having a pliers-like portion with rotatable jaws that bend the wound clips into their clamping configuration.

Surgical clamps differ markedly from surgical staples both in the complexity of their configuration and their mode of forming and implanting. A surgical clamp is of more complex configuration than a surgical staple and is normally bent at its middle portion to clamp it upon the skin of a patient, having small skin engaging tines. A surgical staple, on the other hand, is of much simpler construction and is actually formed so that its legs are implanted in the tissue of a patient.

U.S. Pat. Nos. 4,109,844 and 4,179,057 teach disposable surgical stapling instruments, each provided with an anvil plate terminating in a coextensive anvil surface. Both of these surgical stapling instruments, however, employ a conventional staple former. Such a staple former tends to shear minute particles of the staple during the forming process since, during the staple forming process, the staple is pinched between the former tines and the anvil.

The present invention is directed to a small surgical stapling instrument which may be readily produced as a disposable, single-use instrument. The instrument employs a pair of rotatable formers to cause a surgical staple to be formed without shearing minute particles of the staple during the forming process. The rotatable formers cause portions of the staple to be implanted into the tissue of a patient. The instrument is extremely simple in construction and inexpensive to manufacture. The instrument may have an anvil plate with a coextensive anvil surface so that none of the force required to actuate the pair of rotatable formers is utilized to advance a surgical staple to a proper position for forming. The rotatable formers provide support for the staple as it is formed and placed into the tissue of a patient, thereby permitting the use of finer wire staples than heretofore possible. This, in turn, produces a better cosmetic result.

DISCLOSURE OF THE INVENTION

According to the invention there is provided a disposable surgical stapling instrument for forming and implanting surgical staples in the tissue of a patient. The instrument comprises a body made up of two halves and having a generally triangular configuration. The body has a front face. A lower portion of the body houses a row of staples. An independent feeder assembly is provided to constantly urge the row of staples forwardly so as to locate the forwardmost staple of the row in position to be formed.

A left former and a right former are each pivotally affixed to the front face of the body and are rotatable between normal retracted positions and staple forming positions wherein they form the forwardmost staple of the row.

A spring plate is affixed to the front face of the body and is so configured as to bias the left and right formers to their normal retracted positions. A cover plate is suitably attached to the spring plate and the body so as to complete the front face of the instrument. A left lever and a right lever are pivotally attached to the cover plate and the body and are so configured as to shift the formers to their forming positions, against the biasing action of the spring plate, when a force is applied to the levers to pivot them toward each other. To accomplish this, the device is gripped by the thumb and forefinger of the surgeon on the left lever and right lever. A lug is formed on the inside surface of the cover plate or on the front face of the instrument and is so located as to overlie the crown portion of the forwardmost staple of the row to limit the amount of bending of the crown portion of the forwardmost staple during the staple forming operation.

BRIEF DESCRIPTION OF THE DRAWINGS

FIG. 1 is a side elevational view of the surgical stapling instrument of the present invention.

FIG. 2 is a side elevational view of the surgical stapling instrument illustrating the side opposite that shown in FIG. 1.

FIG. 3 is a front elevational view of the surgical stapling instrument.

FIG. 4 is a rear elevational view of the surgical stapling instrument.

FIG. 5 is a cross sectional view taken along section line 5—5 of FIG. 3.

FIG. 6 is a fragmentary cross sectional view taken along the section line 6—6 of FIG. 5.

FIG. 7 is an exploded prospective view of the surgical stapling instrument of the present invention.

FIG. 8 is a front elevational view of the spring plate of the present invention.

FIG. 9 is a side elevational view of the spring plate, as viewed from the right of FIG. 8.

FIG. 10 is a front elevational view of the surgical stapling instrument with the cover plate and levers removed.

FIG. 11 is a fragmentary front elevational view of the cover plate of the present invention.

FIG. 12 is a fragmentary side elevational view of the cover plate as viewed from the right of FIG. 10.

FIG. 13 is a prospective view of the rear of the cover plate.

FIG. 14 is a front elevational view of the left lever of the surgical stapling instrument.

FIG. 15 is a side elevational view of the lever of FIG. 14, as seen from the right of FIG. 14.

FIG. 16 is a cross sectional view taken along section line 16—16 of FIG. 5.

FIG. 17 is a cross sectional view taken along section line 17—17 of FIG. 5.

DETAILED DESCRIPTION OF THE INVENTION

Figure 18:
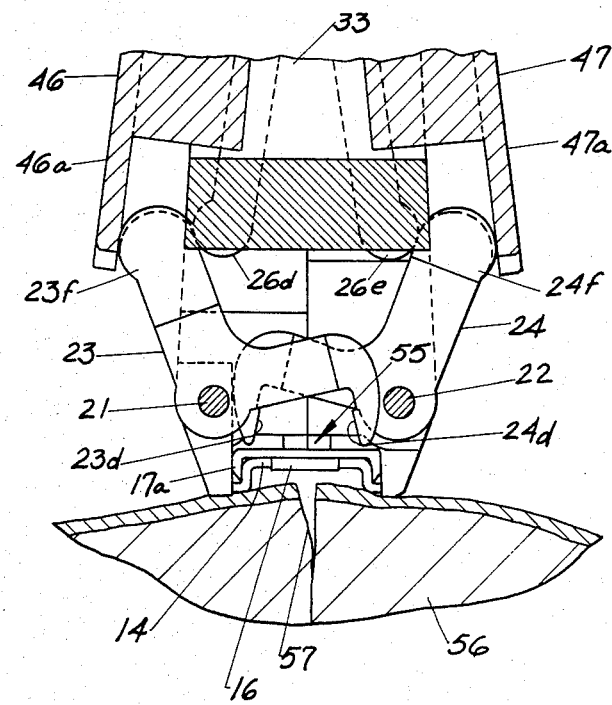
FIG. 18 is a fragmentary cross sectional view, similar to FIG. 16 and illustrating the surgical stapling instrument positioned for implanting and forming a surgical staple to close a wound or incision in a patient's tissue.

For purposes of clarity, throughout all of the Figures, like parts have been given like index numerals. Reference is first made to FIGS. 1 through 4. In these Figures, the instrument is generally indicated at 1. The instrument comprises a pair of body halves 2 and 3 which are substantially identical and which are essentially mirror images of each other. While the body halves may be made of stainless steel or other appropriate material, if the instrument is to be reusable, they lend themselves well to being molded of plastic material suitable for use in a surgical environment and capable of withstanding one or more of the common and well known sterilization procedures. When the instrument is intended to be reusable, the body halves may be joined together by machine screws or other appropriate fastening means (not shown). When the instrument is intended to be disposable, the molded plastic body halves may be joined together by appropriate adhesive means, sonic welding or the like.

It will be evident from FIGS. 1 and 2 that the instrument 1 is generally V-shaped. The lower leg of the V-shaped instrument (as viewed in FIGS. 1 through 4) is generally indicated at 4 and constitutes the magazine portion of the instrument. The nearly upright leg of the V-shaped instrument (as viewed in FIGS. 1 through 4) is generally indicated at 5 and constitutes the actuating portion of the instrument. The leg portions 4 and 5 meet in a nose portion, generally indicated at 6, at which the staples are formed and implanted, as will be apparent hereinafter. Leg portions 4 and 5 are also joined by a web portion generally indicated at 7 for strength, which may be provided with a large circular opening 8, for purposes of material savings.

For a better understanding of the body of the instrument 1, reference is made to FIGS. 5 and 6. FIG. 5 illustrates the body half 2. It will be understood that a description of body half 2 can also serve as a description of body half 3, so long as it is remembered that body half 3 is a mirror image of body half 2.

The body half 2 provides one half 9a of front wall 9 (see also FIGS. 6 and 7). The other half 9b of front wall 9 is provided by body half 3. The front wall 9 constitutes the foundation of the actuation leg 5 of the V-shaped instrument, as will be evident hereinafter. The body half 2 also provides one half 7a of web 7, the other half 7b being provided by body half 3.

Body half 2 provides one half 4a of magazine leg 4, while body half 3 provides the other half 4b thereof. As is clear from FIGS. 5 and 6, the magazine leg 4 is configured to provide two longitudinally extending chambers, an upper chamber 10 and a lower chamber 11. The chambers 10 and 11 are divided from each other by longitudinally extending internal flanges 12a on body half 2 and 12b on body half 3. The flanges 12a and 12b do not meet and therefore define a longitudinally extending slot 13 between chambers 10 and 11. The purpose of slot 13 will be described hereinafter.

The lower chamber 11 is configured to accept an anvil plate 14 of the type taught in U.S. Pat. Nos. 4,109,844 and 4,179,057. Briefly, the anvil plate 14 comprises an elongated metallic member extending the length of lower chamber 11. The anvil plate is generally of inverted U-shaped cross section having an upper planar portion 14a terminating at its longitudinal edges in downwardly depending leg portions 14b and 14c, which, themselves, terminate in laterally extending flanges 14d and 14e (see FIG. 6). The magazine halves 4a and 4b are notched as at 15a and 15b to accept the anvil plate flanges 14d and 14e, respectively. As is most clearly shown in FIG. 5, the upper planar portion 14a of anvil plate 14 terminates at its forward end in a coextensive anvil 16 about which the surgical staples are formed. The anvil 16 is angularly related to the planar upper portion 14a of anvil plate 14 so that when the instrument 1 is being used, the upper or anvil surface of anvil 16 will be substantially parallel to the tissue into which a staple is to be implanted. It will be noted that anvil 16 is located at the nose portion 6 of the instrument.

Anvil plate 14 is straddled by a row of surgical staples. Such a row is shown in FIG. 5 at 17. The forwardmost staple 17a of the row is located on anvil 16 and the rearwardmost staple of the row is shown at 17b. It will be noted that the legs of the surgical staples of the row 17 lie at an angle with respect to the planar portion 14a of anvil plate 14 so as to match the position of the legs of forwardmost staple 17a, as viewed in FIG. 5.

The anvil plate 14 is also straddled by a feeder shoe 18 located behind the row of staples 17. As will be evident from FIG. 6, the feeder shoe 18 has an upper planar portion 18a and downwardly depending sides 18b and 18c. Thus, the feeder shoe 18 has a cross section approximating the shape of the surgical staples. At the forward end of the feeder shoe 18, the forward edges of the feeder shoe sides lie at an angle with respect to the anvil plate 13 equal to the above noted angle of the surgical staple legs. The forward end of feeder shoe side 18b is shown at 18d in FIG. 5. At its rearward end, feeder shoe 18 is provided with an upstanding lug 18e. The lug 18e is operatively connected to one end of a ribbon-like spring 19. At its other end, the spring 19 is coiled within a socket 20 (see FIG. 5) formed in the body halves 2 and 3. It will be evident from FIGS. 5 and 6 that the spring 19 is located in upper chamber 10. The slot or channel 13 between chambers 10 and 11 accommodates the upstanding lug 18e of feeder shoe 18.

The lower chamber 11 of the magazine portion 4 of instrument 1 is so dimensioned as to just nicely accommodate the row of staples 17 and feeder shoe 18 so that both are free to slide along anvil plate 14. The combination of feeder shoe 18 and spring 19 constantly urges the row of staples 17 forwardly, so that the forwardmost staple 17a of the row is located on the upper anvil surface of anvil 16 until the row of staples is depleted. The forwardmost staple 17a of row 17 is supported in place at the front by the cover plate to be described hereinafter and at its rear by the remainder of the staples in the row 17 thereof.

The magazine portion 4 of instrument 1 having been described, the actuating leg or portion 5 will next be set forth. Reference is now made to FIGS. 5 and 7. As indicated above, front wall 9, made up of halves 9a and 9b (of body halves 2 and 3, respectively), constitutes the foundation for the forming leg or portion 5 of the instrument 1. As will be clearly seen in FIGS. 5 and 7, the upper portion of front wall halves 9a and 9b slope downwardly and forwardly, while the lower portions are substantially vertical, as viewed in those Figures. The vertical portions of front wall halves 9a and 9b are provided with pins 21 and 22 (see FIG. 7) by which staple formers 23 and 24, respectively, are rotatively mounted on the vertical portions of front wall halves 9a and 9b.

The staple former 23 comprises an L-shaped element having an upstanding leg 23a and a laterally extending leg 23b. The leg 23b terminates in a downwardly depending hook-like forming end 23c having a forming surface 23d thereon.

The staple former 24 is similar to staple former 23, having an upstanding leg 24a, a laterally extending leg 24b and a hook-shaped downwardly depending forming end 24c with a forming surface 24d thereon. As is shown in FIG. 7, the forming surface 24d may be provided with a longitudinal groove by which it may better support a leg portion of a surgical staple during the forming operation. It will be understood that the forming surface 23d of staple former 23 may similarly be provided with a longitudinally extending groove (not shown).

It will be evident that when staple formers 23 and 24 are mounted on their respective pins 21 and 22, their laterally extending legs 23b and 24b will overlap. This is clearly shown, for example, in FIG. 10. Nevertheless, when the staple formers 23 and 24 are mounted on their respective pins 21 and 22, it is important that their staple forming portions 23c and 24c be coplanar and that their forming surfaces 23d and 24d be opposed when in their full forming positions. To accomplish this, the forming portion 23c of staple former 23 is offset rearwardly as at 23e. Similarly, the forming portion 24c of staple former 24 is offset forwardly as at 24e. Furthermore, the vertical portion of front wall half 9a has a raised portion 25 thereon so as to lie in a plane slightly forward of the plane of the substantially vertical portion of front wall half 9b. This enables the staple formers 23 and 24 to be mounted on their respective pivot pins 21 and 22 in the manner illustrated in FIG. 10.

The upper ends of the upstanding leg portions 23a and 24a of staple formers 23 and 24 are rounded as at 23f and 24f. The upstanding legs 23a and 24a are bent so that their upper rounded portions 23f and 24f lie along the downwardly and forwardly upper sloped portion of front wall halves 9a and 9b. To accommodate for the forwardly extending raised portion 25 on the substantially vertical part of front wall half 9a, the sloped portion of front wall half 9a extends downwardly by a distance slightly greater than the sloped portion of front wall half 9b. To further accommodate for this, the upstanding leg 23a of former 23 is bent at 23g (near the middle of upstanding leg 23a), while the upstanding leg 24a of staple former 24 is bent at 24g, near its rounded end 24f.

FIG. 10 illustrates staple formers 23 and 24 in their normal, unactuated position. The staple formers 23 and 24 are normally maintained in this position by resilient means such as spring plate 26. Spring plate 26 is illustrated in FIGS. 5 and 7 through 10. Spring plate 26 comprises a molded plastic member having an upper body portion 26a and a pair of divergent, downwardly depending, resilient legs 26b and 26c. The legs 26b and 26c terminate in rounded ends 26d and 26e, respectively. The upper body portion 26a of spring plate 26 has a peripheral configuration essentially matching that of the upper portion of front wall 9 (see FIG. 7). The front wall 9 has a pair of perforations 27 and 28 formed therein. The rear surface of spring plate body portion 26a has a pair of integrally formed pins 29 and 30 formed thereon. The pins 29 and 30 on spring plate 26 are adapted to be received in the perforations 27 and 28 of front wall 9 whereby the spring plate 26 is mounted on front wall 9 in the manner shown in FIG. 10. The rounded ends 26d and 26e of spring plate 26 bear against the rounded ends 23f and 24f, respectively, of staple formers 23 and 24 to maintain the staple formers in their normal unactuated position, as shown in FIG. 10. It will be noted that when the spring plate 26 is mounted on the front wall 9a of the instrument body, its legs 26b and 26c are slightly compressed when located between staple formers 23 and 24, as is shown by a comparison of FIGS. 8 and 10. The body portion 26a of spring plate 26 is provided with a second pair of pins 31 and 32 on its forward side. The pin 31 is coaxial with pin 29 as is pin 32 with pin 30. The purpose of forwardly projecting pins 31 and 32 is to mount the cover plate, next to be described.

The cover plate is illustrated in FIGS. 7 and 11 through 13 at 33. Cover plate 33 has an upper portion 33a and a lower portion 33b. The upper portion 33a slopes downwardly and forwardly to conform to the downwardly and forwardly sloping portions of front wall halves 9a and 9b. The front wall lower portion 33b is substantially vertical as viewed in FIGS. 5 and 7, to cover the substantially vertical portions of front wall halves 9a and 9b. Cover plate 33 overlies front wall 9, spring plate 26 and staple formers 23 and 24, serving as the front face of instrument 1.

The upper forwardly and downwardly sloped portion 33a of cover plate 33 is provided with a pair of perforations 34 and 35 adapted to receive the integral pins 31 and 32 of spring plate 26, by which the cover plate is mounted in place. Near its upper end, cover plate 33 is provided with a pair of rounded integral pins 36 and 37, surrounded by annular washer-like surfaces 38 and 39. The purpose of these elements will be described hereinafter. Near the lower end of its portion 33a, the cover plate 33 is provided with another pair of integral pins 40 and 41, again the purpose of which will be apparent hereinafter.

As can be seen in FIGS. 3, 5 and 7, the lowermost end of cover plate 33 is located forwardly of and partially closes the lower chamber 11 of magazine portion 4. The lowermost end of cover plate 33 has a notch 42 formed therein which is so dimensioned as to permit the passage therethrough of the forwardmost surgical staple 17a, only after the surgical staple 17a has been fully formed and implanted. When the instrument is not in use, the forwardmost surgical staple 17a abuts the inside surface 43 (see FIG. 13) of cover plate 33, adjacent notch 42. The lowermost end of cover plate 33 also serves to complete the nose portion 6 of instrument 1.

As is most clearly shown in FIG. 13, the lower, substantially vertical portion 33b of cover plate 33 has a first inside surface 44 and a second inside surface 45. The second inside surface 45 is offset rearwardly with respect to surface 44, lying in a plane parallel to and slightly behind the plane of surface 44. When the cover plate 33 is mounted in place on the instrument 1, staple former pivot pin 21 will abut cover plate inside surface 44 and staple former pivot pin 22 will abut cover plate inside surface 45, the cover plate 33 thereby maintaining staple formers 23 and 24 on their respective pivot pins 21 and 22.

A pair of actuating levers 46 and 47 complete the instrument 1. Levers 46 and 47 are best seen in FIGS. 7 and 14 through 17. Reference is first made to FIGS. 14 and 15 wherein lever 46 is shown. A description of lever 46 can be considered to be a description of lever 47, as well, the lever 47 differing from lever 46 only in that it is a mirror image thereof.

As will be evident from FIGS. 1 through 5 and 17, the lever 46 is intended to be pivotally mounted upon and to straddle the actuating portion or leg 5 of instrument 1. To this end, the lever 46 comprises a side wall 46a of uniform width throughout its length, a front wall 46b slightly wider at its bottom end than in its top end, and a rear wall 46c.

At its upper end, lever front wall 46b has a perforation 48. The rear wall 46c has a coaxial perforation 49 (see FIG. 15). The upper end of lever 46 is pivotally affixed to the instrument. To this end, an integral rounded pin 36 is provided on cover plate 33, as was described with respect to FIGS. 7, 11 and 12. In similar fashion, the rear surface of half 9a of front wall 9 is provided with an integral rounded pin 27 (see FIG. 17) which is coaxial with pin 36. The pin 36 is located in the front wall perforation 48 of lever 46 and the pin 27 is located in the rear wall perforation 49 of lever 46.

It will be noted that rear wall 46c of lever 46 tapers downwardly and outwardly and is shorter than front wall 46b. The rear wall of lever 46 has this configuration so that, when lever 46 is in its actuated condition, rear wall 46c will clear the magazine section 4 and the web 7 of the instrument (see FIG. 4).

To complete lever 46, the inside surface of front wall 46a is provided with an arcuate groove 50. This groove is intended to cooperate with the pin 40 of cover plate 33 to determine the unactuated and actuated positions of lever 46. FIG. 5 shows pin 40 located within groove 50.

As indicated above, lever 47 is a mirror image of lever 46 and comprises a side wall 47a, a front wall 47b and a rear wall 47c (see FIG. 7). The front end rear walls are provided with coaxial perforations 51 and 52 similar to perforations 48 and 49 of lever 46. The lever 47 will be provided with an arcuate groove (not shown) equivalent to the groove 50 of lever 46 and adapted to cooperate with the pin 41 of cover plate 33 to serve the same purpose.

Referring again specifically to FIG. 17, cover plate 33 is provided with a rounded pin 37 equivalent to the pin 36 and previously described with respect to FIGS. 7, 11 and 12. The half 9b of front wall 9 is provided with a coaxial rounded pin 53 on its rear surface. The pins 37 and 53 are located respectively in the perforations 51 and 52 of lever 47 to pivotally affix lever 47 to the actuating portion or leg 5 of the instrument.

Reference is now made to FIG. 16. In FIG. 16, the levers 46 and 47 are shown in their normal, unactuated positions, as are staple formers 23 and 24. It will be noted that the upper rounded ends 23f and 24f of staple formers 23 and 24 contact the inside surfaces of lever side walls 46a and 47a. It will be apparent that if levers 46a and 47a are grasped by the thumb and index finger of the surgeon and are caused to be squeezed toward each other, this will result in the pivoting of formers 23 and 24 to their actuated position against the action of the rounded ends 26d and 26e of spring plate 26. Upon release of the levers, the staple formers 23 and 24 and the levers 46 and 47 will return to their normal positions illustrated in FIG. 16.

The instrument of the present invention may also be provided with certain optional features. First of all, the cover plate 33 may be provided with an arrow-like indicia to aid the surgeon in centering the instrument over the incision or wound to be closed. Such an arrow is shown at 54 on cover plate 33 in FIG. 3. It is also within the scope of the invention to provide a lug on front wall 9 located in parallel spaced relationship to anvil 16. Such a lug is generally indicated at 55 in FIGS. 7 and 16. It will be understood that one half of the lug will be formed on front wall half 9a and the other half of the lug will be formed on front wall 9b. The lug 55 is adapted to overlie the crown portion of the forwardmost surgical staple 17a to minimize bending of the crown during the staple forming and implanting operation. As an alternative, the lug 55 could be formed as an integral part of cover plate 33, located on its inside surface just above notch 42.

Figure 19:
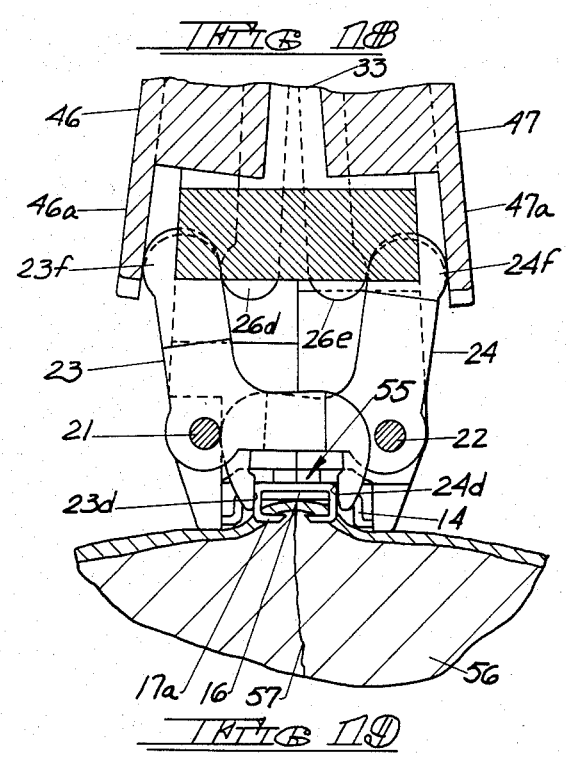
FIG. 19 is a fragmentary cross sectional view, similar to FIG. 18 and illustrating the staple in its fully formed and implanted condition.

The instrument having been described in detail, its operation can be set forth as follows, reference being made to FIGS. 5, 18 and 19 in particular. As indicated above, the row of staples 17 is constantly urged forwardly by the combination of feeder shoe 18 and spring 19 so that a forwardmost staple 17a of the row is always located on anvil 16. The staple is steadied in that position by abutment against the inside surface of cover plate 33 to the front and the remainder of the staple row to the rear. Thus, no effort on the part of the surgeon is required to locate a staple on anvil 16.

The instrument 1 is gripped by the surgeon by locating his thumb and forefinger on levers 46 and 47. The surgeon places the nose portion 6 of the instrument lightly on the tissue to be stapled. This is illustrated in FIG. 18 wherein a patient's tissue is shown at 56 having a wound or incision 57 therein. In FIG. 18, the levers 46 and 47 and the staple formers 23 and 24 are shown in their normal, unactuated positions.

A squeezing motion of the thumb and forefinger of the surgeon causes levers 46 and 47 to begin to rotate toward each other. This, in turn, causes the forming surfaces 23d and 24d of formers 23 and 24 to begin to rotate in a downward path toward anvil 16. As rotation of the formers 23 and 24 continues, frontmost staple 17a of the row 17 is caused to form into a box shape around anvil 16, thereby securely fastening tissue 56 together at the position of wound or incision 57. This is shown in FIG. 19.

When the staple 17a has been fully formed and implanted in the tissue of the patient, the surgeon relaxes the pressure of his thumb and forefinger on levers 46 and 47. Under the urging of the leg ends 26d and 26e of spring plate 26, the staple formers 23 and 24 pivot away from anvil 16 and they and levers 46 and 47 return to their normal positions, as shown in FIG. 18. When the staple formers 23 and 24 have rotated upwardly away from anvil 16 sufficiently, the row of staples 17 under the urging of feeder shoe 18 and spring 19 will advance to position the next staple on anvil 16, ready to be formed and implanted in its turn.

As used herein and in the claims, such words as "upwardly", "downwardly", "laterally" and the like are used in conjunction with the drawings for purposes of clarity of explanation. One skilled in the art will understand that the surgical stapling instrument can be held at any orientation during the staple forming and implanting procedure.

Modifications may be made in the invention without departing from the spirit of it.

What is claimed is:

1. A surgical stapling instrument for forming and implanting surgical staples in the tissue of a patient, said instrument having a supply of surgical staples and an anvil, said surgical stapling instrument having a pair of formers pivotally mounted on said instrument to each side of said anvil for rotation only, said formers being swingable between a normal unactuated position and an actuated position wherein they form a surgical staple about said anvil and implant said surgical staple, each former being so configured as to form said staple about that side of said anvil opposite the side adjacent its pivotal mounting, a pair of levers pivotally mounted on said instrument, each lever contacting one of said staple formers, said levers being manually swingable laterally of said instrument between a normal unactuated position with said staple formers in said unactuated position and an actuated position with said staple formers in said actuated position and a resilient means to bias said staple formers and said levers to their respective unactuated positions.

2. The structure claimed in claim 1 including an anvil plate within said instrument, said anvil plate terminating in said anvil which is coextensive with and an integral part of said anvil plate, a row of staples slidably mounted on said anvil plate and a feeder assembly to constantly urge and advance said row of staples along said anvil plate toward said anvil to locate the forwardmost staple of said row on said anvil to be formed thereabout and implanted by said staple formers.

3. The structure claimed in claim 1 wherein said instrument has a body with a magazine portion and an actuating portion angularly related and meeting in a nose portion, said actuating portion comprising a front wall to which said staple formers are pivotally mounted, an anvil plate mounted within said magazine portion and extending longitudinally thereof, said anvil plate terminating at said instrument nose portion in said anvil which constitutes an integral coextensive part of said anvil plate, a row of staples slidably mounted on said anvil plate and a feeder assembly to constantly urge and advance said row of staples along said anvil plate toward said anvil to locate the forwardmost staple of said row on said anvil to be formed thereabout and implanted by said staple formers.

4. The structure claimed in claim 2 wherein said feeder assembly comprises a feeder shoe and a spring therefor, said feeder shoe being slidably mounted on said anvil plate behind said row of staples, said feeder shoe spring being so configured to constantly urge said feeder shoe along said anvil plate toward said anvil.

5. The structure claimed in claim 3 including a cover plate mounted on said front wall and covering a majority of said staple formers, said cover plate being coextensive with said front wall and having a lower end forming a part of said nose portion, said lower end of said cover plate having a notch formed therein exposing said anvil and being so sized as to permit a fully formed staple to pass therethrough, said lower end of said cover plate serving as a stop for the forwardmost staple of said row prior to the forming thereof.

6. The structure claimed in claim 5 wherein said levers are pivotally affixed to those ends of said cover plate and front wall opposite said nose portion.

7. The structure claimed in claim 5 wherein said staple formers are substantially mirror images of each other, each comprising an L-shaped member having an upstanding leg and a laterally extending leg, said upstanding leg terminating in a rounded, lever-contacting end, said laterally extending legs terminating in a hook-shaped forming portion having a forming surface extending substantially perpendicularly from said laterally extending leg in a direction opposite that of said upstanding leg, said formers being pivoted at the juncture of their upstanding and laterally extending legs to said front wall such that their laterally extending legs overlap with the rounded ends of their upstanding legs each contacting one of said levers, said staple formers when in said unactuated position having their forming surfaces located to either side of and above said anvil and when pivoted to said actuated position having their forming surfaces extending substantially parallel to each other to either side of said anvil with a portion of each forming surface extending below said anvil, said laterally extending stapler former legs being so configured that when said staple formers are in said actuated position said forming portions are coplanar and said forming surfaces are opposed.

8. The structure claimed in claim 7 wherein said resilient means to bias said staple formers and said levers to said unactuated position comprises a spring plate mounted between said front wall and said cover plate, said spring plate having a pair of resilient legs each constantly contacting said rounded end of said upstanding leg of one of said staple formers.

9. The structure claimed in claim 8 wherein said levers are pivotally affixed to those ends of said cover plate and front wall opposite said nose portion.

10. The structure claimed in claim 9 including a lug mounted on one of said front wall and said cover plate, said lug being located in parallel spaced relationship to and above said anvil to minimize bending of the crown portion of the forwardmost staple of said row during the forming and implanting thereof.

* * * * *